(12) United States Patent
Guala

(10) Patent No.: US 7,179,378 B2
(45) Date of Patent: Feb. 20, 2007

(54) TRANSDUCER-PROTECTOR DEVICE FOR BIOMEDICAL HAEMODIALYSIS LINES

(75) Inventor: Gianni Guala, Turin (IT)

(73) Assignee: Industrie Borla S.p.A., Turin (IT)

( * ) Notice: Subject to any disclaimer, the term of this patent is extended or adjusted under 35 U.S.C. 154(b) by 464 days.

(21) Appl. No.: 10/747,151

(22) Filed: Dec. 30, 2003

(65) Prior Publication Data

US 2004/0173516 A1 Sep. 9, 2004

(30) Foreign Application Priority Data

Apr. 3, 2003 (IT) .......................... TO2003A0257

(51) Int. Cl.
*B01D 29/00* (2006.01)
*B01D 63/00* (2006.01)

(52) U.S. Cl. ...................... 210/232; 210/445; 210/446; 210/238; 210/321.71; 604/126; 604/252

(58) Field of Classification Search ................ 210/232, 210/445, 446, 451, 453, 455, 454; 604/126, 604/252; 55/495, 503, 511, 491, 497, 502, 55/510; 95/45; 96/4

See application file for complete search history.

(56) References Cited

U.S. PATENT DOCUMENTS

| 4,077,882 A | | 3/1978 | Gangemi | |
|---|---|---|---|---|
| 4,326,957 A | * | 4/1982 | Rosenberg | ................... 210/436 |
| 6,086,762 A | * | 7/2000 | Guala | .......................... 210/232 |

FOREIGN PATENT DOCUMENTS

EP 0 887 085 A2 12/1998

* cited by examiner

*Primary Examiner*—Krishnan S. Menon
(74) *Attorney, Agent, or Firm*—Sughrue Mion, PLLC

(57) ABSTRACT

Transducer-protector device for biomedical haemodialysis lines comprising a first and a second element each of which is formed in a single piece of moulded plastic material with a tubular fitting and an annular radial flange. The first element is formed with a semi-crystalline polymer and the related annular radial flange has greatly thinner portions able to allow the see-through viewing of the filtering membrane secured between the flanges of the first and of the second element.

16 Claims, 2 Drawing Sheets

TRANSDUCER-PROTECTOR DEVICE FOR BIOMEDICAL HAEMODIALYSIS LINES

BACKGROUND OF THE INVENTION

The present invention relates to transducer-protector devices for biomedical haemodialysis lines, comprising:
- a first element including in a single piece of moulded plastic material a tubular fitting of the female Luer Lock type, designed to be connected with a tubing of a haemodialysis machine, and an annular radial flange,
- a second element including in a single piece of moulded thermoplastic material a tubular fitting and an annular radial flange permanently joined in sealed fashion to said annular radial flange of the first element with said tubular fittings arranged coaxially, and
- a filtering membrane made of permeable material defining a sterile anti-contamination barrier, peripherally secured between said annular radial flanges.

Such transducer-protector devices must have meet two fundamental requirements: in the first place, they must assure, in use, a perfect and total hermetic seal between the first tubular fitting and the tubing of the haemodialysis machine on one side, and the second tubular fitting and the line connected to the patient on the other side. In the second place, they must be sterilisable by any traditional system, and in particular by means of steam treatment. For this reason, the plastic materials whereof the first and the second element of the device are formed must have such characteristics as to assure the necessary structural and dimensional stability even when heated to the steam sterilisation temperature. Otherwise, any deformations of one and/or of the other radial flange could cause an incomplete securing of the peripheral edge of the filtering membrane between the two flanges and, consequently, the ineffectiveness of the sterile barrier which said membrane should instead assure.

STATE OF THE PRIOR ART

Traditionally, the second element of the device is formed with highly rigid thermoplastic material, normally polycarbonate, which has the additional advantage of being transparent and hence of making visible the membrane from the exterior, thus allowing to detect any traces of blood.

On the other hand the connection between the female Luer Lock tubular fitting of the first element and the tubing of the haemodialysis machine is normally achieved through a metallic male Luer connector joined to said tubing. This tubing must be perfectly hermetic, and any imperfections, however small, may lead to fluid leaks which are absolutely unacceptable. For this reason, use of a highly rigid thermoplastic material to form the first element of the device, for instance the same material used to form the second element, is not practicable as would instead be desirable both to support the operations for the steam sterilisation of the device, and to allow the see-through viewing of the membrane.

The European Patent EP-B-0887085 by the same Applicant proposes to form the first element of the transducer-protector device with a relatively elastic thermoplastic material, i.e. with better elasticity characteristics than polycarbonate. More in particular, the European patent EP-B-0887085 proposes to use, to form the first element of the device, a polymer of poly-butylenterephtalate, and more specifically the one called Vestodur, manufactured and marketed by Hüls. This material assures the necessary elasticity to guarantee, in use, a perfectly hermetic connection between the tubular fitting of the first element and the metallic connector of the haemodialysis machine, and it is also able to guarantee the necessary structural stability of the related annular flange even at high temperature, i.e. in the case of steam sterilisation of the transducer-protector device.

However, an unsolved problem is that of guaranteeing the visibility from outside the membrane, from the side of the first element of the device, for the required checks, since the first element of the transducer-protector device in accordance with the teachings of the patent EP-B-0887085 does not allow to obtain this effect.

SUMMARY OF THE INVENTION

The object of the present invention is to overcome the aforesaid drawback.

According to the invention, this object is achieved thanks to the fact that the thermoplastic material of the aforesaid first element of the transducer-protector device is a semi-crystalline polymer and the aforesaid annular radial flange of said first element has at least a portion with greatly reduced thickness relative to the general thickness of said flange, and transparent, in order to allow the vision of said membrane from outside said first element.

In this way, the visibility of the membrane can be assured both from the side of the first, and on the side of the second element of the transducer-protector device.

The aforesaid greatly reduced thickness may be in the order of a few tens of millimetres, for instance around 0.3 mm.

According to a preferred embodiment of the invention, the portion with reduced thickness is formed by a crown of transparent radial sections arranged coaxially around the tubular fitting of the first element, and said radial sections are mutually separated by radial baffles which are integral with said flange and whose thickness is substantially equal to the general thickness thereof.

The semi-crystalline polymer for moulding the first element of the transducer-protector device according to the invention can be selected in the class of poly-butylenterephtalate polymers, or in the class of polyamides or in the class of polyolephins.

Unlike the case of amorphous polymers, whose isotropic structure allows light fully to travel through them without refraction effects, making said polymers transparent or anyway translucid in practice, in the case of semi-crystalline polymers there are more or less extensive areas where the related chains are arranged in orderly fashion, but they are embedded within an amorphous basic matrix. Said crystalline islands refract light homogeneously within the structure of the polymer, hence their opacity.

In the fluid state, all polymers are in substantially amorphous conditions, due to the high molecular agitation induced by temperature. If during the injection moulding process one succeeds with appropriate measures to "freeze" the structure of the semi-crystalline polymer in an amorphous state without allowing the creation and spreading of the crystalline areas, a nearly transparent semi-crystalline polymer can be obtained. Since crystallisation is linked to the heat evacuation rate, this effect is all the more pronounced when the thickness of the moulded piece is reduced, because the heat conductivity of plastic materials is very low.

The invention thus makes available a transducer-protector device which on one hand fully meets mechanical requirements in relation to the connection between the first element and the tubing of the haemodialysis machine and on the other hand assures full visibility from the exterior of the filtering membrane for necessary checks.

BRIEF DESCRIPTION OF THE DRAWINGS

The invention shall now be described with reference to the accompanying drawings, provided purely by way of non limiting example, in which.

DETAILED DESCRIPTION OF THE INVENTION

Figure 1:
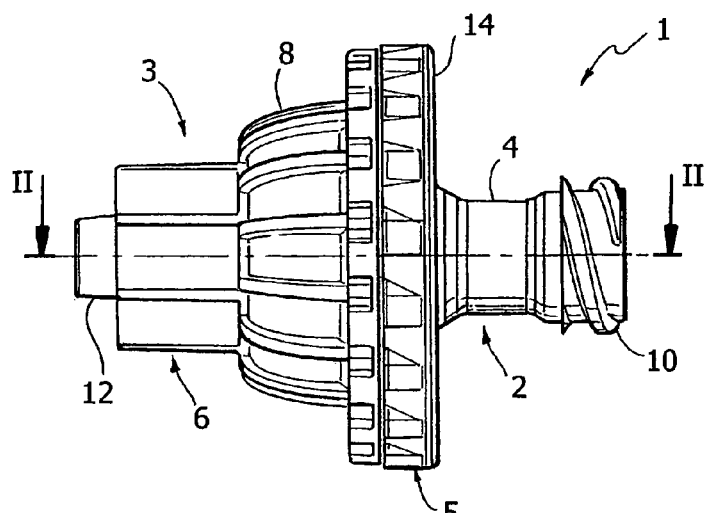
FIG. 1 is a schematic side elevation view of a transducer-protector device according to the invention.

In the drawings, the reference number 1 globally designates a transducer-protector device according to the invention, destined to be inserted in a biomedical haemodialysis line.

The transducer-protector device 1 comprises a first element 2 and a second element each of which is formed by a single piece of moulded thermoplastic material.

The first element 2 includes a tubular fitting 4, destined in use to be connected with a tubing of a haemodialysis machine, and an annular radial flange 5.

Similarly, the second element 3 comprises a tubular fitting 6 destined in use to be connected to a tubing going to a patient subjected to haemodialysis, and a radial annular flange 7 joined to the tubular fitting 6 through an enlarged part 8 with grip tabs.

The two annular flanges 5, 7 are frontally coupled to each other, with the tubular junctions 4 and 6 arranged coaxially, and they are permanently connected in sealed fashion for instance by ultrasonic welding. A filtering membrane made of permeable material 9 (FIGS. 2 and 5) is interposed between the annular flanges 5, 7 with its own outer peripheral edge mechanically fastened between corresponding frontal areas of the two flanges 5, 7.

The membrane 9 defines a sterile anti-contamination barrier between the tubular fittings 4 and 6.

Figure 2:
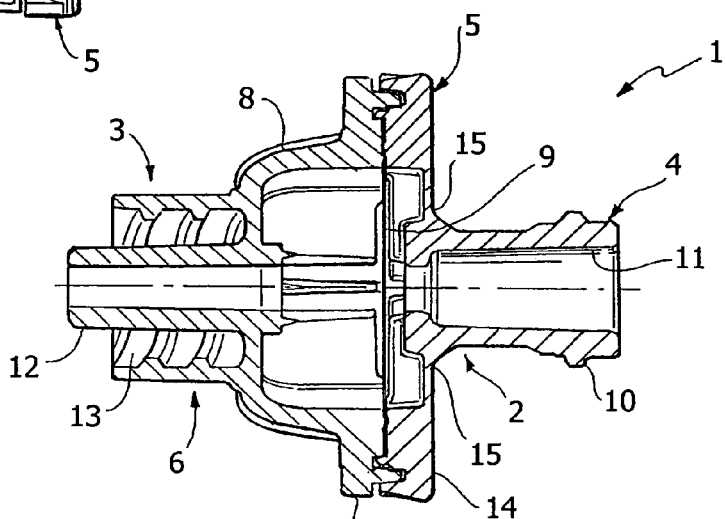
FIG. 2 is a longitudinal section view according to the line II—II of FIG. 1.
Figure 3:
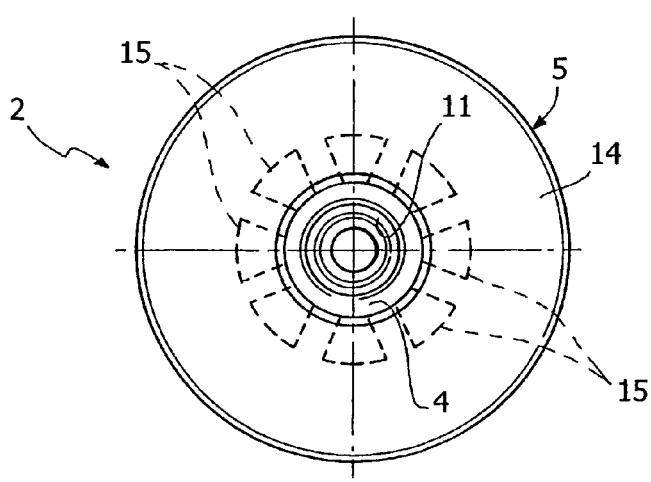
FIG. 3 is an elevation view showing the exterior part of the first element of the transducer-protector device
Figure 4:
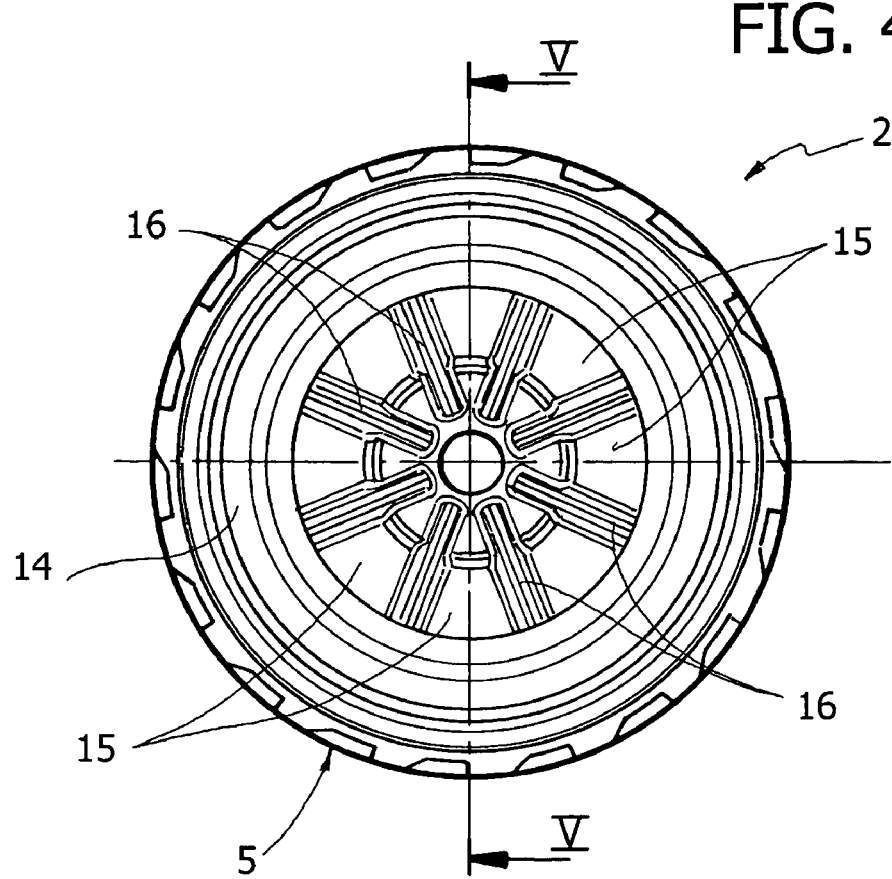
FIG. 4 is an enlarged elevation view showing the interior part of the first element of the transducer-protector device, e
Figure 5:
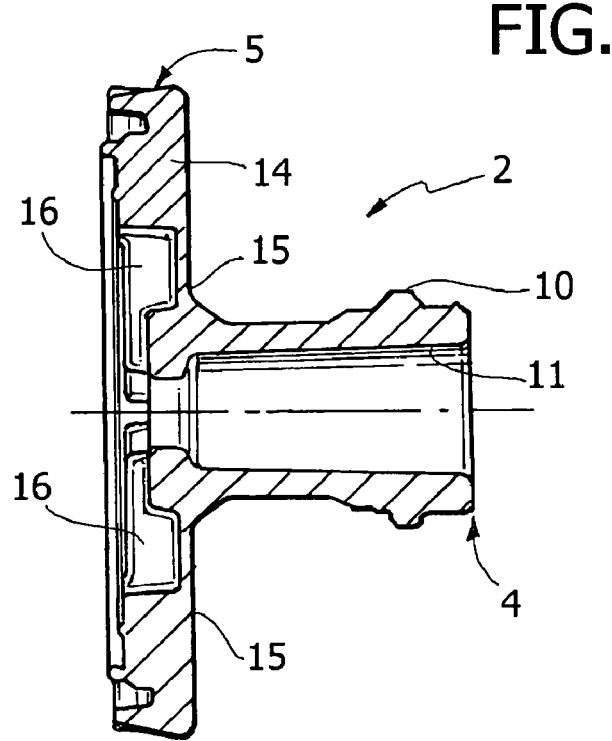
FIG. 5 is a cross section view according to the line V—V of FIG. 4.

The tubular fitting 4 of the first element 2 is of the female Luer Lock type and, as shown in FIGS. 2 and 5, it is formed with an outer thread 10 and with a conical inner surface 11 diverging outwardly. The particular conformation of said tubular fitting 4 is conveniently the one described in detail in the aforementioned European patent EP-B-0887085.

The tubular fitting 6 of the second element 3 is formed in the manner of a male Luer Lock connector, with an inner tubular part 12 and an internally threaded hollow external cladding 13.

The second element 3 is formed by injection moulding a high strength and high rigidity material, normally polycarbonate, which also has the characteristic of being transparent. This assures a complete visibility from the exterior of the filtering membrane 9 from the side of the second element 3.

Instead of polycarbonate, a polyamide can be used, in particular nylon 6, or also polypropylene.

For the injection moulding of the first element 2, according to a first aspect of the invention, a semi-crystalline polymer is used, typically selected in the class of polymers of poly-butylenterephtalate (in particular Vestodur), or in the class of polyamides (for example nylon 6) or else in the class of polyolephins (in particular, polypropylene).

According to another aspect of the invention, the annular radial flange 5 of the first element 2 is formed with at least a portion with greatly reduced thickness relative to the general thickness of said flange 5. The term "general thickness" herein means the thickness of the radially outermost peripheral band of the flange 5, designated by the number 14 in FIGS. 2 and 5: by way of example said thickness may be in the order of 1.2–1.6 mm, for example about 1.4 mm.

The portion with greatly reduced thickness is in fact formed by a crown of radial section 15 formed between the outer peripheral band 14 and the inner end of the tubular fitting 4, coaxially thereto. The thinner sections 15 are mutually separated by radial baffles 16 formed integrally to the flange 5 and whose axial thickness is substantially equal to the thickness of the peripheral band 14.

As stated previously, the thickness of the thinner sections 15 is greatly reduced relative to the thickness of the peripheral band 14 of the flange 5, and it is for example in the order of ¼–⅕ thereof. Thus, if the thickness of the peripheral band 14 is in the order of 1.4 mm, the thickness of the sections 15 will be in the order of 0.3 mm.

Taking into account the characteristics of the semi-crystalline polymer that constitutes the entire first element 2 and the greatly reduced thickness of the sections 15, the sections 15 define transparent windows. As a result of the injection moulding process of the first element 2, the reduced thickness of the sections 15 causes the structure of the semi-crystalline polymer to remain, in the areas of said sections 15, in an amorphous i.e. lacking crystalline areas. Since the crystallisation of the polymer is linked to the rate of evacuation of the heat as a result of the moulding process, this effect will be all the more pronounced the more reduced the thickness of the thinner sections 15, though of course compatibly with the necessary mechanical strength requirements.

In this way, the filtering membrane 9 will be clearly visible from the outside, not only from the side of the second element 3, but also from the side of the first element 2 through the transparent thinner sections 15.

As stated previously, the currently preferred combination of thermoplastic for forming the first element 2 and the second element 3 of the transducer-protector device 1 is, respectively, Vestodur and polycarbonate. Other suitable combinations are polycarbonate-nylon, nylon-nylon, polycarbonate-polypropylene, polypropylene-polypropylene.

Naturally, the construction details and the embodiments may vary widely from what is described and illustrated purely by way of example herein, without thereby departing from the scope of the present invention as defined in the appended claims.

I claim:

1. Transducer-protector device for biomedical haemodialysis lines comprising:
   a first element including in a single piece of moulded thermoplastic material a tubular fitting of the female Luer Lock type, designed to be connected to a tubing of a haemodialysis machine, and an annular radial flange,
   a second element including in a single piece of moulded thermoplastic material a tubular fitting and an annular radial flange permanently joined in sealed fashion to said annular radial flange of the first element with said tubular fittings arranged coaxially, and a filtering membrane of permeable material defining a sterile anti-contamination barrier peripherally secured between said annular radial flanges, wherein the thermoplastic material of said first element is a relatively elastic material, and wherein:

said thermoplastic material of said first element is a polymer with a semi-crystalline structure and a structure that remains in an amorphous state in a portion of said annular radial flange of the first element that has a greatly reduced thickness to an extent such as to be transparent, thereby allowing the vision of said membrane from the exterior of said first element.

2. A device as claimed in claim 1, wherein said reduced thickness is a fraction of the general thickness of said flange.

3. A device as claimed in claim 2, wherein said reduced thickness is between 0.2 and 0.5 mm and is conveniently in the order of 0.3 mm.

4. A device as claimed in claims 1, wherein said portion with reduced thickness is formed by a crown of transparent radial sections arranged coaxially around the tubular fitting of said first element.

5. A device as claimed in claim 4, wherein said transparent radial sections are mutually separated by radial baffles integral with said flange (5) and whose thickness is substantially equal to the general thickness thereof.

6. A device as claimed in claim 1, wherein said polymer is selected in the class of poly-butylenterephtalate polymers.

7. A device as claimed in claim 1, wherein said polymer is selected in the class of polyamides.

8. A device as claimed in claim 1, wherein said polymer is selected in the class of polyolephins.

9. A method for forming a transducer-protector device for biomedical per biomedical haemodialysis lines comprising the following steps:

providing a first element formed in a single piece of moulded thermoplastic material with a tubular fitting of the female Luer Lock type, designed to be connected to a fitting of a haemodialysis machine, and with an annular radial flange, providing a second element formed in a single piece of moulded thermoplastic material with a tubular fitting and with an annular radial flange, permanently joining together in sealed fashion said flanges with said tubular fittings arranged coaxially, and with a filtering membrane made of permeable material defining a sterile anti-contamination barrier peripherally secured between said annular radial flanges, wherein the thermoplastic material of said first element is a relatively elastic material and the thermoplastic material of said second element is substantially transparent, and wherein said first element is formed of a semi-crystalline polymer with a semi-crystalline structure and a structure that remains in an amorphous state in radial sections, of said annular radial flange of the first element, said radial sections having a greatly reduced thickness such as to be transparent, in order to allow the see-through viewing of said membrane from the exterior of said element.

10. A method as claimed in claim 9, wherein said reduced thickness is a fraction of the general thickness of said flange.

11. A method as claimed in claim 9, wherein said reduced thickness is between 0.2 and 0.5 mm and conveniently in the order of 0.3 mm.

12. A method as claimed in claim 9, wherein said portion with reduced thickness is formed by a crown of transparent radial sections arranged coaxially around the tubular fitting of said first element.

13. A method as claimed in claim 9, wherein between said transparent radial sections are formed, integrally with said flange, integral radial separating baffles whose thickness is substantially equal to the general thickness thereof.

14. A method as claimed in claim 9, wherein said polymer is selected in the class of poly-butylenterephtalate polymers.

15. A method as claimed in claim 9, wherein said polymer is selected in the class of polyamides.

16. A method as claimed in claim 9, wherein said polymer is selected in the class of polyolephins.

* * * * *